United States Patent
Prinz et al.

(10) Patent No.: US 8,962,014 B2
(45) Date of Patent: Feb. 24, 2015

(54) TRANSDERMAL THERAPEUTIC SYSTEM FOR ADMINISTERING RIVASTIGMINE OR DERIVATIVES THEREOF

(75) Inventors: Heike Prinz, Unterhaching (DE); Björn Schurad, München (DE); Thomas Beckert, Birkenhard (DE); Kristina Linder, Kiefersfelden (DE)

(73) Assignee: Acino AG, Miesbach (DE)

( * ) Notice: Subject to any disclaimer, the term of this patent is extended or adjusted under 35 U.S.C. 154(b) by 23 days.

(21) Appl. No.: 13/518,006

(22) PCT Filed: Dec. 14, 2010

(86) PCT No.: PCT/EP2010/069654
§ 371 (c)(1),
(2), (4) Date: Oct. 23, 2012

(87) PCT Pub. No.: WO2011/076621
PCT Pub. Date: Jun. 30, 2011

(65) Prior Publication Data
US 2013/0261571 A1    Oct. 3, 2013

(30) Foreign Application Priority Data

Dec. 22, 2009   (EP) .................................... 09180413
Feb. 25, 2010   (EP) .................................... 10154648

(51) Int. Cl.
*A61F 13/00*   (2006.01)
*A61K 9/70*    (2006.01)
*A61K 31/27*   (2006.01)

(52) U.S. Cl.
CPC ......... *A61F 13/00063* (2013.01); *A61K 9/7084* (2013.01); *A61K 31/27* (2013.01); *A61F 13/00991* (2013.01)
USPC ........... 424/449; 514/476; 514/490; 514/649; 514/654; 562/493

(58) Field of Classification Search
USPC .................. 424/449; 514/476, 490, 649, 654; 562/493
See application file for complete search history.

(56) References Cited

U.S. PATENT DOCUMENTS

| | | | |
|---|---|---|---|
| 5,602,176 A | 2/1997 | Enz | |
| 6,335,031 B1 | 1/2002 | Asmussen et al. | |
| 6,689,379 B1 | 2/2004 | Bracht | |
| 2004/0086552 A1* | 5/2004 | Klokkers et al. | 424/449 |
| 2004/0241219 A1* | 12/2004 | Hille et al. | 424/449 |
| 2007/0259028 A1* | 11/2007 | Ito | 424/449 |
| 2008/0044461 A1* | 2/2008 | Valia et al. | 424/449 |
| 2011/0059141 A1 | 3/2011 | Ito | |

FOREIGN PATENT DOCUMENTS

| | | | |
|---|---|---|---|
| EP | 1 047 409 | 7/1999 | |
| GB | 2 203 040 A | 10/1988 | |
| JP | H 63-307818 A | 12/1988 | |
| JP | H 01-233212 A | 9/1989 | |
| JP | H 08-193030 A | 7/1996 | |
| JP | H 10-152434 A | 6/1998 | |
| JP | 2003 313 122 A | 11/2003 | |
| WO | WO 99/34782 A1 | 7/1999 | |
| WO | WO 02/03969 A2 | 1/2002 | |
| WO | WO 03/017988 A1 | 3/2003 | |
| WO | WO 2007/064407 A1 | 6/2007 | |
| WO | WO2007064407 A1 * | 6/2007 | A61K 9/70 |

OTHER PUBLICATIONS

PCT/EP2010/069654—International Search Report, Nov. 2, 2011.
PCT/EP2010/069654—International Written Opinion, Nov. 2, 2011.
PCT/EP2010/069654—International Preliminary Report on Patentability, Jul. 10, 2012.
English language translation of Japanese Office Action for corresponding Japanese Application No. 2012-545226, mailed on Sep. 24, 2014.

* cited by examiner

*Primary Examiner* — Jane C Oswecki
(74) *Attorney, Agent, or Firm* — Curatolo Sidoti Co., LPA; Joseph G. Curatolo; Salvatore A. Sidoti

(57) ABSTRACT

The present invention relates to a transdermal therapeutic system for administering an active substance through the skin, comprising:
 a) a cover layer,
 b) a reservoir present on the cover layer, comprising a polymer matrix comprising the active substance,
 c) an adhesive layer present on the reservoir comprising a contact adhesive, and
 d) a removable layer present on the adhesive layer,
the active substance being rivastigmine, a physiologically compatible salt, hydrate, solvate or derivative thereof, characterized in that the polymer matrix of the reservoir comprises neither hydroxyl groups nor carboxyl groups.

20 Claims, No Drawings

TRANSDERMAL THERAPEUTIC SYSTEM FOR ADMINISTERING RIVASTIGMINE OR DERIVATIVES THEREOF

CROSS REFERENCE TO RELATED APPLICATIONS

This application is a national stage application of International Application No. PCT/EP2010/069654, filed 14 Dec. 2010, which claims priority from European Patent Application No. 09180413.8, filed 22 Dec. 2009, and from European Patent Application No. 10154648.9, filed 25 Feb. 2010, from which applications priority is claimed, and which are incorporated herein by reference.

The present invention relates to a system for the transdermal administration of rivastigmine or a physiologically compatible salt, hydrate, solvate or derivative thereof for therapeutic purposes.

Rivastigmine is the phenyl carbamate (S)—N-ethyl-3-[(1-dimethylamino)ethyl]-N-methyl-phenyl-carbamate of formula I.

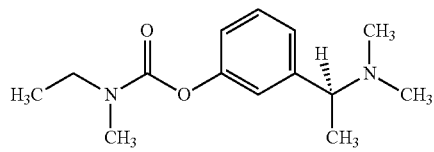

It is a cholinesterase inhibitor acting on the central nervous system and, therefore, an active substance for treating Alzheimer's and Parkinson's dementia.

Rivastigmine can be present as a free base, but also as an acid addition salt, hydrate, solvate or another derivative. Unless indicated otherwise, said derivatives shall be comprised in the designation "rivastigmine" for purposes of the present invention.

A preferred administration form of rivastigmine is the percutaneous administration route by means of a transdermal therapeutic system, meaning a transdermal patch. Typically, a transdermal patch is a self-adhesive bandage that contains the active substance to be administered. These bandages can have different shapes and sizes. The simplest type is an adhesive monolith that comprises a supply of active substance (reservoir) on a carrier (cover layer). The reservoir is typically constituted of the active substance in a pharmaceutically acceptable, pressure-sensitive adhesive and is in contact with the surface of the skin, whereby the active substance is released into the body of the patient by means of transdermal diffusion.

More complex patches are multi-laminates or patches with an active substance supply that can have a further adhesive layer disposed between the reservoir and the skin.

One administration form of rivastigmine by means of a transdermal patch has been specified previously in the basic patent on rivastigmine, which is GB 2203040. The transdermal patch disclosed therein consists of a cover layer and a layer constituting the reservoir. Aside from the active substance rivastigmine, the reservoir contains a hydrophilic polymer, non-swelling acrylate polymer and an emollient.

After the publication of GB 2203040, further transdermal therapeutic systems (TTS) containing, among others, rivastigmine as active substance, have been developed and described. WO 02/03969 specifies a TTS in which the matrix layer comprising the active substance (reservoir) also contains, in addition, highly dispersed silicon dioxide to increase skin permeation.

In DE 199 18 106, the reservoir contains a contact-adhesive polymer that includes acrylic acid or methacrylic acid units of a defined carboxyl group content, indented to improve the absorbency of water as well as the tolerance of acidic polyacrylic contact adhesives relative to moisture.

WO 2007/064407 A1 discloses a TTS having a silicone-based adhesive layer intended to improve the adhesive properties, tolerance and safety of rivastigmine therapy. According to WO 2007/064407 A1, it is especially preferred for the reservoir layer to contain an antioxidant (page 7, paragraph 4). Correspondingly, all formulations in the examples contain the antioxidant vitamin E. The trade product Durotak® 387-2353 that is used therein is a polyacrylate with carboxyl groups. WO 2007/064407 A1 provides that the reservoir layer also include different substances to improve penetration such as, for example, glycerin, fatty acids (page 7, paragraph 5). Most of the time, these substances contain free hydroxyl or carboxyl groups, which are thus also present in the polymer matrix of the reservoir layer. WO 2007/064407 A1 does not specifically address the stability of rivastigmine. In particular, WO 2007/064407 A1 does not teach how to select certain polymers for the polymer matrix of the reservoir layer to prevent the rivastigmine from being broken down.

US 2008/0044461 A1 discloses TTS formulations with donepezil (see examples). Rivastigmine is mentioned as well (Claim 7). US 2008/0044461 A1 does not disclose an active-substance layer having a polymer matrix. Rather, the release mechanism is controlled by means of a membrane (so-called membrane patches), not by a polymer backbone that has the active substance embedded therein (so-called matrix patch). Moreover, one essential characteristic of US 2008/0044461 A1 provides that the reservoir can contains a gelatinizing agent and a permeation enhancer (see Claim 1). Alcohols are used as permeation enhancers (see [0053]). Cellulose polymers are used as gelatinizing agents (see [0055]). Therefore, the permeation enhancers as well as the gelatinizing agents are compounds with free hydroxyl groups that are present in the TTS in the reservoir layer.

US 2007/0259028 A1 discloses TTS formulations with donepezil (see examples). Rivastigmine is mentioned as well (Claim 3). One essential characteristic of US 2007/0259028 A1 provides that the reservoir layer contain a polyvalent alcohol such as, for example, glycerin. According to US 2007/0259028 A1, free hydroxyl groups are necessarily present in the polymer matrix of the reservoir layer.

US 2004/0086552 A1 discloses TTS formulations with an active substance that can be selected from a very long list (see [0070] to [0095]). Disclosed are matrix patches as well as "membrane patches" (see [0057] and/or [0058]). Regarding matrix patches, US 2004/0086552 A1 does not teach selecting certain polymers for the matrix to stabilize the active substance.

U.S. Pat. No. 6,689,379 B1 discloses TTS formulations having a special adhesive layer. Rivastigmine is also mentioned as a possible active substance. Preferably, the active-substance layer is to contain a compound with hydroxyl groups, see Claim 10. U.S. Pat. No. 6,689,379 B1 does not teach selecting certain polymers for the polymer matrix of the reservoir layer to prevent the rivastigmine from breaking down.

However, patent EP 1 047 409, on the other hand, reports a general problem associated with the administration of rivastigmine by means of a TTS. It was found that the active substance tends to degrade especially in the presence of oxygen. According to EP 1 047 409, in the transdermal composition that is disclosed in GB 2203040, rivastigmine degrades despite the formation of a closed polymer matrix surrounding the active substance and air-tight packaging of the composition. EP 1 047 409 resolves the problem of the poor stability of rivastigmine by adding an antioxidant to the pharmaceutical composition.

Therefore, it is the object of the present invention to provide therapeutic compositions containing rivastigmine for transdermal administration that demonstrate adequate stability even without the addition of antioxidants.

Surprisingly, it was found that rivastigmine in transdermal patches has adequate stability if the polymer matrix of the reservoir contains neither hydroxyl groups nor carboxyl groups. The present invention is based, among other aspects, on selecting special polymers for the polymer matrix to thereby prevent and/or minimize the break-down of rivastigmine.

The present invention, correspondingly, provides a TTS that demonstrates adequate stability and contains rivastigmine, as well as a method for preparing the same. Moreover, the invention envisions the use of polymers or copolymers, which contain neither hydroxyl groups nor carboxyl groups, inside a TTS containing rivastigmine, as well as a TTS for treating Alzheimer's and Parkinson's dementia.

Therefore, a first aspect of the invention consists in providing a TTS for administering rivastigmine comprising the following components:
a) a cover layer,
b) a reservoir present on the cover layer, comprising a polymer matrix with the embedded active substance, and wherein the active substance is rivastigmine or a physiologically compatible salt, hydrate, solvate or derivatives thereof,
c) an adhesive layer on the reservoir comprising a first polyisobutylene polymer of a mean molecular weight between 30,000 g/mol and 100,000 g/mol and a second polyisobutylene polymer of a mean molecular weight between 300,000 g/mol and 500,000 g/mol, and
d) a removable layer present on the adhesive layer characterized in that the polymer matrix of the reservoir includes neither hydroxyl groups nor carboxyl groups.

A second aspect of the invention is a TTS for administering rivastigmine comprising the following components:
a) a cover layer,
b) a reservoir present on the cover layer, comprising a polymer matrix comprising the embedded active substance,
c) an adhesive layer present on the reservoir comprising a contact adhesive, and
d) a removable layer present on the adhesive layer,
and wherein the active substance is rivastigmine or a physiologically compatible salt, hydrate, solvate or derivative thereof, and wherein the polymer matrix of the reservoir includes neither hydroxyl groups nor carboxyl groups.

A "polymer matrix" is a solid or semi-solid composition having a three-dimensional structure comprising a polymer or polymer mixture. The polymer matrix is also referred to as the polymer backbone because the polymer or polymer mixture typically provides the three-dimensional backbone structure. The polymer matrix can also have further substances such as, for example, an active substance that is embedded therein. Preferably, the active substance is evenly distributed throughout the polymer matrix. A person skilled in the art will be familiar with so-called "matrix patches" in which the polymer matrix is the control mechanism for the release of the active substance.

In the TTS according to the invention, the active substance rivastigmine demonstrates adequate stability. "Adequate stability" herein means that contaminations of the active substance after one month of storage at 40° C. and 75% relative humidity are overall no more than 1 weight %, preferably no more than 0.5 weight %, in relation to the desired active-substance content in the formulation. Contaminations of the active substance in the formulation are defined herein as degradation products of the active substance rivastigmine and any contaminations that entered the formulation together with the active substance (for example, intermediate product traces from the preparation of the active substance).

The stability and/or the quantity of contaminants can be detected as described in the example. Preferably, the total content of degradation products/contaminations after three months of storage at 40° C. and 75% relative humidity should be 1 weight % or less, more preferably less than 0.6 weight %. It is also preferred that the total content of the degradation products/contaminations after six months of storage at 40° C. and 75% relative humidity is less than 1 weight %. It is further preferred that the total content of contaminations after one month of storage at 25° C. and 60% relative humidity is less than 0.25 weight %. Also preferred, furthermore, is that the total content of contaminations after three and after six months of storage at 25° C. and 60% relative humidity is less than 0.5 weight %. The information as to "weight %" of contaminations always refers to the desired active-substance content in the formulation, unless indicated otherwise.

The length of application of the TTS according to the invention is, preferably, approximately 24 hours. A longer application is possible.

Preferably, an antioxidant is not be added to any component of the TTS. However, it is quite possible for antioxidants to be available in the present invention, provided they do not negatively impact the mode of action of the TTS. To be noted herein is the fact that antioxidants are not necessary to stabilize rivastigmine according to the present invention. Antioxidants could, however, also be used for other purposes than the above purpose in the context of the TTS according to the invention. Therefore, it is possible, although not preferred, for the TTS according to the invention to contain antioxidants.

An "antioxidant" within the meaning of the present invention is a pharmaceutically compatible compound or composition that decelerates, inhibits, interrupts and/or stops oxidation processes. Antioxidants include, in particular, the following substances: tocopherols and the esters thereof, sesamol of sesame oil, coniferyl benzoate of benzoin resin, nordihydroguaietic resin and nordihydroguaiaretic acid (NDGA), gallates (among others, methyl, ethyl, propyl, amyl, butyl, lauryl gallates), butylated hydroxyanisole (BHA/BHT, also butyl-p-cresol); ascorbic acid and salts and esters thereof (for example, acorbyl palmitate), erythorbinic acid (isoascorbinic acid) and salts and esters thereof, monothioglycerol, sodium formaldehyde sulfoxylate, sodium metabisulfite, sodium bisulfite, sodium sulfite, potassium metabisulfite, butylated hydroxyanisole, butylated hydroxytoluene (BHT), propionic acid. Typical antioxidants are tocopherol such as, for example, α-tocopherol and the esters thereof, butylated hydroxytoluene and butylated hydroxyanisole. The terms "tocopherol" also includes esters of tocopherol. A known tocopherol is α-tocopherol. The term "α-tocopherol" includes esters of α-tocopherol (for example, α-tocopherol acetate).

Preferably, the reservoir, more preferred the entire TTS, does not contain any tocopherol. In a further embodied example, the reservoir, preferably the entire TTS, does not contain any tocopherol and nor any butylated hydroxyanisole (BHA/BHT, also butyl-p-cresol). In a further embodied example, the reservoir, preferably the entire TTS, does not contain any tocopherol, nor any butylated hydroxyanisole, nor any butylated hydroxytoluene. In a special embodied example, the reservoir, preferably the entire the TTS, does not contain any of the following antioxidants: tocopherol and the esters thereof, sesamol of sesame oil, coniferyl benzoate of benzoin resin, nordihydroguaietic resin and nordihydroguaiaretic acid (NDGA), gallates (among others, methyl, ethyl, propyl, amyl, butyl, lauryl gallates), butylated hydroxdyanisole (BHA/BHT, also butyl-p-cresol); ascorbinic acid and salts thereof, ascorbyl palmitate, erythorbinic acid (isoascorbinic acid) and salts and esters thereof, monothioglycerol, sodium formaldehyde sulfoxylate, sodium metabisulfite, sodium bisulfite, sodium sulfite, potassium metabisulfite, butylated hydroxyanisole, butylated hydroxytoluene, propionic acid. In special preferred example, the reservoir, more preferred the entire TTS, does not contain any antioxidants.

The antioxidant quantity in the TTS of the present invention is usually less than 1 weight % or less than 0.1 weight-%, more preferred less than 0.05 weight-%, most preferred less than 0.01 weight-%, respectively in relation to the weight of the total formulation (without cover layer and removable layer).

The structure of the TTS according to the invention comprises multiple layers. A cover layers is located at the end of the TTS that comes to lie opposite to the skin during application. The reservoir is located on the side of the cover layer that is directed toward the human skin during use. In addition, the adhesive layer is located on the side directed toward the human skin during use. Before the application, a removable layer is located on the side that is directed toward the human skin and that is pulled off immediately before use of the US.

The area of the TTS according to the invention is not subject to any special limitations. Usually the area is 5 to 30 cm² in size; however, larger or smaller sizes are possible.

The area of the cover layer of the TTS according to the invention corresponds in one embodied example at least to the area of the reservoir and/or the adhesive layer. However, it can be larger than the area of the reservoir, whereby the reservoir is fully covered with the cover layer extending even beyond the edge of the reservoir. However, in such an embodied example, either the area of the adhesive layer should be equal to the area of the cover layer, or the layer of the cover layer that is directed toward the skin should have a further adhesive layer in order to ensure that, during the application, the entire surface of the TTS that is directed toward the skin adheres to the skin. In another embodied example, the cover layer is somewhat smaller than the area of the reservoir.

Reservoir

The reservoir layer of the TTS according to the invention has the active substance rivastigmine embedded in a polymer matrix. According to this aspect of the invention, the polymer matrix consists exclusively of polymers or copolymers that do not include any hydroxyl groups, nor any carboxyl groups. Preferred polymers or copolymers without functional groups constituting the polymer matrix are certain polyacrylates, acrylate-vinyl acetate copolymers, polyisobutylene and styrene-butadiene copolymers than can be present individually or as a mixture.

Possible for use as expedient polyacrylates, essentially not containing any free functional groups, are polymers (homopolymers, copolymers and block copolymers) on the basis of acrylic acid esters and/or methacrylic acid esters. Suitable monomer alternatives for the preparation of expedient polyacrylates are, in particular, n-butyl acrylate, n-butyl methacrylat, ethyl acrylate, 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate and mixtures of these monomers. These monomers are esters of acrylic and/or methacrylic acid carrying linear, branched or cyclic aliphatic $C_1$-$C_{12}$ substituents, without having any other free functional groups. Vinyl acetate, as well, can be used as a co-monomer together with at least one of these monomers for the preparation of the polyacrylate.

Preferably, the polymer matrix consists of one or several polyacrylates that essentially do not contain any free functional groups. More preferred, the polymer matrix consists of polyacrylates that were prepared by polymerizing acrylic acid esters and/or methacrylic acid esters. In a special embodied example, the polymer matrix consists of polyacrylates that were obtained by polymerizing acrylic acid esters and/or methacrylic acid esters, and wherein the acrylic acid esters and/or methacrylic acid esters are selected from the group consisting of n-butyl acrylate, n-butyl methacrylate, ethyl acrylate, 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate and mixtures thereof. In another embodied example, the polymer matrix consists essentially of polyacrylates that were prepared by copolymerizing acrylic acid esters and/or methacrylic acid esters with vinyl acetate, and wherein the acrylic acid esters and/or methacrylic acid esters were selected from the group consisting of n-butyl acrylate, n-butyl methacrylate, ethyl acrylate, 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate and mixtures thereof.

Especially preferred are as follows: the acrylate-vinyl acetate copolymer Duro-Tak® 87-4098, prepared, respectively, at approximately 50% of starting monomers 2-ethylhexyl acrylate and vinyl acetate; the acrylate Duro-Tak® 87-9088 (also an acrylate polymer without functional groups) available from the company Henkel. In a special embodied example, the acrylate Duro-Tak® 87-900A or Duro-Tak® 87-9301 is used for the polymer matrix.

The total proportion of monomers containing free hydroxyl groups or free carboxyl groups (for example, acrylic acid, methacrylic acid and esters of acrylic acid and/or methacrylic acid carrying functional groups, in particular esters containing hydroxyl groups) is less than 1 weight %, preferably less than 0.5 weight %, more preferred less than 0.2 weight %, in relation to the monomer mixture from which the polymer matrix is prepared. In one special embodied example, the total proportion of these monomers is less than 0.1 weight %. In one special embodied example, the monomer mixture does not contain any free hydroxyl groups, nor any free carboxyl groups.

A TTS that contains polyacrylates as polymer matrix with active-substance content being free of hydroxyl groups and carboxyl groups has been described previously in WO 03/017988 A1; however, not in connection with rivastigmine as active substance. The task to be achieved as specified in WO 03/017988 was to describe a remedy for the disadvantage of poor utilization of the active substance within a TTS. According to said disclosure, this object was achieved by polymer matrixes that were ideally completely free of hydroxyl groups or carboxyl groups. The active substance rivastigmine is not mentioned in this specification, nor any action for improving the stability of rivastigmine.

In one embodied example of the invention, the reservoir is essentially without polymers or copolymers that contain any free hydroxyl groups or free carboxyl groups. Preferably, the reservoir contains neither any free hydroxyl groups nor any free carboxyl groups. More preferred, the reservoir essentially does not contain any free amino groups, nor any free hydroxyl groups, nor any free carboxyl groups. In a special embodied example, the adhesive layer is essentially also free of polymers or copolymers containing any free hydroxyl groups or any free carboxyl groups. Preferably, the adhesive layer does not contain any free hydroxyl groups, nor any free carboxyl groups. More preferred, the adhesive layer does not contain any free amino groups, nor any free hydroxyl groups, nor any free carboxyl groups.

Preferably, the reservoir contains 20 to 40 weight % rivastigmine and 60 to 80 weight % polymer matrix in relation to the total weight of the reservoir layer. In a special embodied example of the TTS, the reservoir contains 25 weight % rivastigmine and 75 weight % polymer matrix. Preferably, the reservoir has no further components in addition to the active substance and the polymer matrix. However, it is possible for further additives known from the prior art to be present in the reservoir. For example, emollients or gelatinizing agents can also be present in the reservoir.

The absolute quantity of rivastigmine depends on different factors, in particular the size of the TSS to be used, the weight per unit area and the concentration of the active substance within the reservoir. The weights per unit area of dried reservoir matrix are, preferably, in the range of 20 to 100 g/m², more preferred in a range of 25 to 80 g/m², and even more preferred in a range of 30 to 70 g/m². The reservoir can have a thickness (dry thickness) in the range of 20 to 400 µm, or 30 to 200 µm, or 40 to 100 µm. Other thicknesses than those mentioned above are also possible.

Adhesive Layer

The adhesive layer of the TTS according to the invention contains a contact adhesive, preferably consisting of polyisobutylene. Polyisobutylene is a pressure-sensitive contact adhesive that does not set and, therefore, maintains its adhesive properties over long periods of time. Preferably, polyisobutylenes having differing mean molecular weights are used by way of a mixture. Polyisobutylene is available in different mean molecular weights. The term "mean molecular weight" in connection with polyisobutylene in the context of the present application refers to the so-called viscosity-average molecular weight, $M_V$. The viscosity-average molecular weight $M_V$ is determined from the solution viscosity of a solution of polyisobutylene in isooctane at 20° C. The measuring instrument is an Ubbelohde's viscometer. The average viscosity is calculated using the formula below:

$$M_V = 0.65\sqrt{\frac{J_0 \times 10^2}{3.06}}$$

The Staudinger index $J_o$ of intrinsic viscosity that is necessary for the determination of the viscosity-average molecular weight $M_V$ is obtained according to the Schulz-Blaschke relationship from the measured specific viscosity $\eta_{SP}$ and the concentration of the solution.

$$J_o = \eta_{SP}/c(1+0.31\times\eta_{SP}) cm^3/g \quad \text{(Schulze-Blaschke relationship)}$$

The specific viscosity $\eta_{SP} = t/t_0 - 1$, wherein t and $t_0$ are the flow time of the solution and/or solvent (with Hagenbach-Couette correction, respectively), and c is the concentration of the solution in g/cm³. If necessary, regulation DIN 53728 can be used as well in a supplementary fashion.

Expedient mean molecular weights $M_V$ of polyisobutylene are, for example, in the range from approximately 40,000 g/mol to approximately 4,000,000 g/mol. One preferred mixture consists of (1) polyisobutylene having a mean molecular weight $M_V$ of approximately 40,000 g/mol (for example, Oppanol® B10, available from the company BASF) and (2) polyisobutylene having a mean molecular weight $M_V$ of above approximately 1,000,000 g/mol (for example, Oppanol® B100, available from BASF, of a mean molecular weight $M_V$ of approximately 1,110,000 g/mol). It is within the expert knowledge of a person skilled in the art to mix the different molecular weights at expedient ratios in order to obtain the desired properties for the adhesive layer.

The polyisobutylene in the adhesive layer can include a molecular weight distribution having a first relative maximum between 30,000 g/mol and 100,000 g/mol and a second relative maximum between 300,000 g/mol and 500,000 g/mol. More preferred, the first relative maximum is between 35,000 g/mol and 50,000 g/mol and the second relative maximum, independently thereof, between 350,000 g/mol and 450,000 g/mol. Most preferred, the first relative maximum is approximately at 40,000 g/mol and, independently thereof, the second relative maximum is approximately at 400,000 g/mol.

The polyisobutylene mixture of the contact adhesive can be obtained by mixing a first polyisobutylene polymer of a mean molecular weight $M_V$ between 30,000 g/mol and 100,000 g/mol with a second polyisobutylene polymer of a mean molecular weight $M_V$ of between 300,000 g/mol and 500,000 g/mol. The first polyisobutylene polymer, preferably, has a mean molecular weight $M_V$ in the range between 35,000 g/mol and 50,000 g/mol, most preferably a value of approximately 40,000 g/mol. The second polyisobutylene polymer, preferably, has a mean molecular weight $M_V$ in the range between 350,000 g/mol and 450,000 g/mol, most preferably a value of approximately 400,000 g/mol.

The most preferred mixture is that of (1) polyisobutylene of a mean molecular weight $M_V$ of approximately 40,000 g/mol (for example, Oppanol® B10 SFN, available from BASF) and (2) polyisobutylene of a mean molecular weight $M_V$ of approximately 400,000 g/mol (for example, Oppanol® B50 SF, available from BASF).

The proportions at which the two polyisobutylene polymers are present within the mixture can vary. The weight ratio of the first polyisobutylene polymer relative to the second polyisobutylene polymer in the mixture can be from 10:1 to 1:10, preferably it is 2:1 to 1:2; the most preferred weight ratio is 4:6. In a special embodied example, the polyisobutylene polymer of the contact adhesive consists of four weight parts Oppanol® B10 (for example, Oppanol® B10 SFN) and six weight parts Oppanol® B50SF.

The contact adhesive is present in the adhesive layer according to the invention at a quantity that is in the range of 40 to 100 weight %, preferably 50 to 90 weight %, more preferred at 55 to 80 weight % and even more preferred 60 to 69.9 weight % in relation to the total weight of the adhesive layer.

The thickness of the adhesive layer (dry thickness) is not subject to any special limitations. It can be in the range of approximately 10 to 300 µm or in the range between 70 to 140

μm. The absolute quantity of the adhesive layer can be approximately 10 to 50 g/m² or 20 to 40 g/m², without being limited thereto.

Preferably, the adhesive layer further contains emollients and gelatinizing agents. Expedient emollients are known from the prior art; preferably, these are mineral oil, neutral oil, paraffin, polybutenes, linseed oil, octyl palmitate, squalene, squalane, silicone oil, isobutyl myristate, isostearyl alcohol and/or oleyl alcohol, especially preferred are mineral oil, neutral oil, polybutenes and/or paraffin. Mineral oil are colorless, clear hydrocarbons. They are obtained from the distillation fractions of raw oil that boil above approximately 300° C. and are freed of any solid hydrocarbons by cooling. Utilizing expedient fractioning, it is possible to obtain mineral oils that are liquid at body temperature, meaning approximately 35 to 37° C., while they are solid at lower temperatures, in particular temperatures below 20° C. Selecting a mineral oil with a melting point of approximately 30 to 35° C. is preferred. Paraffin and mineral oils that are in compliance with the requirements of Ph. Eur. 6 and/or USP 32-NF 27 are especially preferred.

Preferably, the emollient is present in the adhesive layer at a quantity in the range from 0 to 60 weight %, more preferred in the range from 10 to 50 weight %, even more preferred in the range of 25 to 39.9 weight %, for example 35 weight %, in relation to the total weight of the adhesive layer.

The gelatinizing agent is preferably a gelatinizing agent of a particle structure having on its surface a high concentration of polar groups. The same create correspondingly high interfacial surface tensions that are in part compensated by agglomeration of the particles into gel skeletons. Correspondingly, the greater the polarity difference between the oils and the surface of the skeleton former, the more solid are the gel skeletons. Preferably, the invention provides for the use of highly dispersed silicone dioxide or pyrogenic silicic acid. The size of the particles is, preferably, in the nanometer range such as, for example in the range of 400 to 1500 nm, especially in the range of 500 to 1000 nm. Pyrogenic silicic acid is sold, for example, under the trade name CAB-O-SIL® and is a known thickening agent for mineral oil. A further example of an expedient gelatinizing agent is bentonite. Also possible is the use of sodium carbomer that is known in the art as a gelatinizing agent. Preferably, the gelatinizing agent is used at a quantity of 0.1 to 4.0 weight %, more preferred at 0.1 to 2.0 weight %, even more preferred at 0.5 to 2.0 weight %, in relation to the weight of the adhesive layer.

In an especially preferred embodied example of the TTS according to the invention, the adhesive layer contains 60 to 69.9 weight % contact adhesive, and/or polyisobutylene, and wherein the same, as described above, can consist of polyisobutylene mixtures of different molecular weights, 0.1 to 2.0 weight % gelatinizing agent, and/or highly dispersed silicone dioxide or pyrogenic silicic acid, and 25 to 39.9 weight % emollient, and/or mineral oil, in relation to the total weight of the adhesive layer.

Preferably, the cover layer of the TTS according to the invention is of an occlusive nature, meaning it closes off the system. In a preferred embodied example, such cover layers can consist of polyolefins, particularly polyethylene, or of polyesters as well polyurethanes. Layers containing several polymers disposed one on top of the other are also advantageously usable. Expedient materials comprise polyolefin, cellophane, cellulose acetate, ethyl cellulose, emollient-provided vinyl acetate-vinyl chloride copolymers, ethylene-vinyl acetate copolymers, polyethylene therephtalate, nylon, polyethylene, polypropylene, polyvinylidene chloride, ethylene-methacrylate copolymers, paper that can be coated, if necessary, textile fabrics, aluminum foil and composite polymer metal materials. Especially preferred are polyester films, such as polyethylene therephtalate films. The thickness of the backing can be for example 10 μm to 100 μm, as is common in the prior art such as, for example, approximately 40 μm (nominal thickness). Very especially preferred are film-based dressings made of pigmented PE, PETP and aluminum.

According to the invention, a removable layer is located on the adhesive layer, also referred to as the "release liner." This removable layer is preferably manufactured of a polymer material that can be metalized, if necessary. Examples of preferably used materials are polyurethanes, polyvinyl acetate, polyvinylidene chloride, polypropylene, polycarbonate, polystyrene, polyethylene, polyethylene therephtalate, polybutylene therephtalate as well as paper that is surface-coated with the corresponding polymers, if necessary. Preferably, this is a one-sided or two-sided siliconized or fluoropolymer-coated removable layer. Especially preferred are commonly available fluoropolymer-coated or siliconized polyester films such as, for example, the one-sided, siliconized trade products Primeliner 100 μm and Perlasic LF 75 μm (by the companies Loparex, NL and Perlen Converting AG, Switzerland) or the one-sidedly fluoropolymer-coated products such as, for example, ScotchPak 1022 (3M Drug delivery).

An especially preferred embodied example of the TTS according to the invention is a TTS for administering an active substance through the skin comprising:
  a) a cover layer,
  b) a reservoir located on the cover layer containing 20 to 30 weight % active substance and 70 to 80% polymer matrix in relation to the total weight of the reservoirs, and wherein the polymer matrix consists essentially of an acrylate-vinyl acetate copolymer without hydroxyl groups and without carboxyl groups, and wherein the active substance is rivastigmine or a physiologically compatible salt, hydrate, solvate or derivative thereof,
  c) an adhesive layer located on the reservoir that comprises 0.1 to 1 weight % silicone dioxide, 25 to 39.9 weight % of a light mineral oil (paraffinum perliquidum) and as contact adhesive 60 to 79.9 weight % of a mixture of a polyisobutylene polymer of a mean molecular weight $M_V$ of approximately 40,000 g/mol and a polyisobutylene polymer of a mean molecular weight $M_V$ of approximately 400,000 g/mol; and
  d) a removable layer located on the adhesive layer,
and wherein the quantity of antioxidant in the total formulation, without cover and removable layer, is less than 0.1 weight %, preferably less than 0.01%.

In one special embodied example, the TTS according to the invention does not contain an antioxidant that is selected of the group consisting of vitamin E and esters thereof, butylated hydroxytoluene and butylated hydroxyanisole.

A third aspect of the present invention is a transdermal therapeutic system for administering an active substance through the skin comprising:
  a) a cover layer,
  b) a reservoir located on the cover layer comprising a polymer matrix containing the active substance,
  c) an adhesive layer located on the reservoir comprising a contact adhesive, and
  d) a removable layer located on the adhesive layer;
and wherein the active substance is rivastigmine or a physiologically compatible salt, hydrate, solvate or derivative thereof, characterized in that the TTS does not contain any antioxidants.

Preferably, the polymer matrix of the reservoir (of the TTS as set forth in the third aspect according to the invention) contains neither hydroxyl groups nor carboxyl groups. The embodied examples as described above with regard to the first and/or second aspect of the invention apply correspondingly for the third aspect without any need for reiterating them.

A forth aspect of the present invention consists in providing a method for preparing the TTS according to the invention. The method comprises:

i) preparing a component containing the reservoir made up of the cover layer and the reservoir, which is located on the side of the cover layer that is intended as the side to be directed toward the skin;

ii) preparing a component containing the adhesive layer made up of the removable layer and the adhesive layer located on the removable layer; and iii) laminating to combine the components from i) and ii) so that in the end, in the cross-section of the completed TTS, the cover and removable layers constitute the outermost, opposite layers.

A preferred embodied example of this method comprises i) applying, with drying, if necessary, a film of a composition constituting the reservoir, if necessary, in form of a solution or dispersion in a suitable medium to the side of the cover layer that is to be directed toward the skin and, if necessary, coating with a siliconized removable film (liner); or applying and subsequent drying, if necessary, of a film constituting the composition of the reservoir, if necessary, in form of a solution or dispersion in a suitable medium, to a siliconized removable film (liner) and coating with a cover layer;

ii) applying, with subsequent drying, if necessary, a film of a composition constituting the adhesive layer, if necessary, in the form of a solution or dispersion in a suitable medium, to the removable layer; and iii) laminating together the components from i) and ii), if necessary, removing the liner in order for the cover layer and the removable layer to constitute in the cross-section of the completed TTS the outermost, opposite layers.

The preparation of a preferred TTS can be achieved by first dispersing and/or dissolving the components for the reservoir, meaning rivastigmine and the matrix-forming polymer and/or copolymer or a mixture thereof, in an organic solvent such as heptane or ethyl acetate (provided the polymer is not already available in a dissolved form). The matrix-forming polymer and/or copolymer or the mixture thereof is/are usually already available in a solvent. According to the invention, a polymer and/or copolymer is/are used as defined in connection with the TTS according to the invention above, meaning a polymer and/or copolymer without hydroxyl groups and without carboxyl groups. The embodied examples of the polymer matrix, which are mentioned above as preferred, apply correspondingly for the method according to the invention. A volatile organic solvent is preferably used in the preparation of the reservoir. This mixture is then applied in an even layer to the cover layer and dried. Preferably, to protect it, the component for the reservoir is provided with a film, preferably a siliconized polyester film, which is also referred to as an "intermediate liner" and is applied to the side of the reservoir that is opposite to the cover layer. In the alternative, and/or as an equivalent, it is possible to apply the mixture initially to the "intermediate liner" and dry it, and wherein the cover layer is then applied to the side of the reservoir located opposite of the "intermediate liner." The "intermediate liner" is removed shortly before the reservoir component is combined with the component containing the adhesive layer.

The adhesive layer is prepared in a separate work step by dispersing the polymer mixture constituting the contact adhesive (dissolved in an organic solvent), preferably polyisobutylene of different mean molecular weights, together with the gelatinizing agent and the emollient in an organic solvent, such as heptane. However, preferably, the contact adhesive and the emollient are dissolved in an organic solvent and, subsequently, the gelatinizing agent is dispersed in this solution. This mixture is then applied to the removable film and allowed to dry.

The components obtained in the two method steps are subsequently laminated together; specifically, in such a way that the adhesive layer is directly applied to the reservoir. The finished laminated film pieces can afterwards be punched into the desired sizes and packaged.

The organic solvents that are needed for the individual method steps in order to dissolve the respective components in solution and/or to disperse them are removed by exposing the products to increasing temperatures, if necessary including the application of a vacuum.

A fifth aspect of the present invention constitutes the use of a polymer or copolymer in the context of a rivastigmine-containing TTS that includes neither hydroxyl groups nor carboxyl groups. Preferred are polyacrylates, acrylate-vinyl acetate copolymers, polyisobutylene and styrene-butadiene copolymers. According to the invention, these polymers or copolymers represent the polymer matrix in which the active substance rivastigmine is embedded.

Preferably, the use according the invention envisions polyacrylates and polyacrylate copolymers that are free of any hydroxyl groups and any carboxyl groups, such as acrylate-vinyl acetate copolymers.

An especially preferred embodied example according to the invention uses acrylate-vinyl acetate copolymer Duro-Tak® 87-4098.

A sixth aspect of the present invention envisions providing the TTS according to the invention for treating Alzheimer's and Parkinson's dementia. The TTS according to the invention is preferably prepared for an application period of approximately 24 hours.

Preferred embodied examples of the TTS according to the invention shall be described in further detail below; in addition, the properties of said embodied examples in terms of stability shall be determined.

EXAMPLES

Examples 1

Preparation of the Different Formulations

Four different batches A-D of TTS formulation containing rivastigmine base were prepared. Acrylate-vinyl acetate copolymer was used as matrix-forming polymer for the reservoir. An overview of the components of the different batches is compiled in Table 1.

TABLE 1

Composition of Batches A to D

| Batch | | Composition |
|---|---|---|
| A | | 30% rivastigmine base |
| | | 70% Duro-Tak ® 87-4098 |
| B | Reservoir: | 30% rivastigmine base |
| | | 70% Duro-Tak ® 87-4098 |
| | Adhesive layer: | 30% Klearol ® |
| | | 1% Cab-O-Sil ® |
| | | 69% Oppanol ® B10/B100 (7/3) |

TABLE 1-continued

Composition of Batches A to D

| Batch | Composition | |
|---|---|---|
| C | Reservoir: | 20% rivastigmine base |
|   |            | 80% Duro-Tak ® 87-4098 |
|   | Adhesive layer: | 30% Klearol ® |
|   |                 | 0.5% Cab-O-Sil ® |
|   |                 | 69.5% Oppanol ® B10/B100 (7/3) |
| D | Reservoir: | 25% rivastigmine base |
|   |            | 75% Duro-Tak ® 87-4098 |
|   | Adhesive layer: | 30% Klearol ® |
|   |                 | 1% Cab-O-Sil ® |
|   |                 | 69% Oppanol ® B10/B100 (7/3) |

The components used in the batches can be described in more detail as follows:

TABLE 2

Component Overview of Formulation Examples A to D

| Component Name | Chemical Description | Function |
|---|---|---|
| Duro-Tak ® 87-4098 | Acrylate/vinyl acetate copolymer | Matrix polymer |
| Cab-O-Sil ® | Pyrogenic silicone dioxide | Gelatinizing agent |
| Klearol ® | Light mineral oil | Emollient |
| Oppanol ® B10 | Polyisobutylene ($M_w = 4 \times 10^4$ g/mol) | Contact adhesive |
| Oppanol ® B100 | Polyisobutylene ($M_w = 1.1 \times 10^6$ g/mol) | Contact adhesive |

Preparation Method

1. Preparation of the Reservoir Layer

The acrylate-vinyl acetate adhesive is provided and rivastigmine and ethyl acetate are weighed in. Then the components are mixed in a sufficient quantity of ethyl acetate by means of an agitator until a spreadable, homogenous coating mass is achieved.

The homogenous coating mass is applied to a siliconized film ("intermediate liner") as a thin film layer. The matrix film is dried at 60° C./20 min and 80° C./5 min, then coated with a cover layer of PET.

2. Preparation of the Adhesive Layer and the Total Laminate

The polyisobutylene adhesives are weighed in together, then mixed. Subsequently, while stirring, Heptan, Klearol® and Cab-O-Sil® are added. Stirring is continued until a homogenous mass is obtained.

The mass is applied to a removable layer ("release liner") as a thin film, then the solvents are drawn off at 60° C./20 min and 80° C./5 min. After drying, the laminate is coated with the reservoir layer, wherein the "intermediate liner" is removed first.

Patches of expedient sizes are punched from the laminate.

Stability Tests

The batches A and B were subjected to stability tests. To this end, the punched-out TTS were sealed in aluminum foil bags and stored for one month at 25° C. and 60% relative humidity; respectively, at 40° C. and 75% relative humidity. Afterwards, the extent of the contaminations that may have formed due to the degradation of rivastigmine was determined by means of HPLC and UV absorption. The results of these tests are compiled in Table 3.

TABLE 3

| Batch | Contamination | | Storage |
|---|---|---|---|
|  | 25° C./60% rel. hum. | 40° C./75% rel. hum. |  |
| A | RT = 46 min: 0.18% | — | Initially |
|   | Total: 0.18% |  |  |
|   | RT = 46 min: 0.22% | RT = 46 min: 0.29% | 1 month |
|   | Total: 0.22% | Total: 0.29% |  |
| B | RT = 46 min: 0.34% | RT = 46 min: 0.35% | 2 weeks |
|   | Total: 0.34% | Total: 0.35% |  |
|   | RT = 46 min: 0.36% | RT = 46 min: 0.38% | 1 month |
|   | Total: 0.36% | Total: 0.38% |  |

The found contamination is indicated by its respective retention time (RT). The percentage amount of contamination is the proportion of the total weight of the involved formulations. The lower limit of the indicated measured values RL (Reporting Limit) is 0.1% because all values there-below are in the range of measuring inaccuracy.

The results of this study clearly show that the TTS formulations according to the invention demonstrate adequate stability. In all formulation examples, the contamination RT=46 min after one month at 40° C. and 75% relative humidity is below 0.4%.

Example 2

Preparation of Different Formulations

Two different batches of TTS formulations containing rivastigmine base were prepared. Acrylate vinyl-acetate copolymer was used as matrix-forming polymer for the reservoir. An overview as to the components of the different batches is shown in Table 4.

TABLE 4

Composition of Batches 179/181 and 179/182:

| Batch | Composition | |
|---|---|---|
| 179/181 | Reservoir: | 25% rivastigmine base |
|         |            | 75% Duro-Tak ® 87-4098 |
|         | Adhesive layer: | 30% Pionier ® 7028P (Hansen & Rosenthal) |
|         |                 | 0.5% Cab-O-Sil ® |
|         |                 | 69.5% Oppanol ® B10 SFN/B50 SF (4/6) |
| 179/182 | Reservoir: | 25% rivastigmine base |
|         |            | 75% Duro-Tak ® 87-4098 |
|         | Adhesive layer: | 35% paraffin, thin-fluid (Merck) |
|         |                 | 0.5% Cab-O-Sil ® |
|         |                 | 64.5% Oppanol ® B10 SFN/B50 SF (4/6) |

The components used in the batches can be described in more detail as follows:

TABLE 5

Component Overview of Formulation Examples

| Component Name | Chemical Description | Function |
|---|---|---|
| Duro-Tak ® 87-4098 | Acrylate/vinyl-acetat copolymer | Matrix polymer |
| Cab-O-Sil ® | Pyrogenic silicone dioxide | Gelatinizing agent |
| Pionier ® 7028P | Light mineral oil (paraffinum perliquidum) | Emollient |
| Oppanol ® B10 SFN | Polyisobutylene ($M_\gamma$ = ca. 4 × $10^4$ g/mol) | Contact adhesive |
| Oppanol ® B50 SF | Polyisobutylene ($M_\gamma$ = ca. 4 × $10^5$ g/mol) | Contact adhesive |

Preparation Method

1. Preparation of the Reservoir Layer

The acrylate-vinyl acetate adhesive is provided and rivastigmine and ethyl acetate are weighed in. Then the components are mixed in a sufficient quantity of ethyl acetate by means of an agitator until a spreadable, homogenous coating mass is achieved.

The homogenous coating mass is applied to a siliconized film ("intermediate liner") as a thin film. The matrix film is dried at 60° C./20 min and 80° C./5 min, then coated with a cover layer of PET.

2. Preparation of the Adhesive Layer and the Total Laminate

The polyisobutylene adhesives are weighed in together, then mixed. Subsequently, while stirring, heptane, Pionier® 7028P/paraffin oil (thin liquid) and Cab-O-Sil® are added. Stirring is continued until a homogenous mass is obtained.

The mass is applied to a removable layer ("release liner") as a thin film, then the solvents are drawn off at 60° C./20 min and 80° C./5 min. After drying, the laminate is coated with the reservoir layer, wherein the "intermediate liner" is removed first.

Patches of expedient sizes are punched from the laminate.

Stability Tests

Batches A and B were subjected to stability tests. In this context, the punched-out TTS were sealed in aluminum foil bags and stored for one month at 25° C. and 60% relative humidity; respectively, at 40° C. and 75% relative humidity. Afterwards, the extent of contamination that may have formed due to the degradation of rivastigmine was determined by means of HPLC and UV absorption. The results of these tests are compiled in Tables 6 and 7.

[Glossary for Tables 6 and 7]
Table 6: Contaminations in Formulation 179/181
Initial=initially
Monat=month
Monate=months
Table 7: Contaminations in Formulation 179/182
Initial=initially
Monat=month
Monate=months

TABELLE 6

Verunreinigungen in Formulierung 179/181

| | | 1 Monat | | 3 Monate | | | 6 Monate | |
|---|---|---|---|---|---|---|---|---|
| Initial | 25° C. | 40° C. | 5° C. | 25° C. | 40° C. | | 25° C. | 40° C. |
| Imp 1: <RL | Imp 1: <RL | Imp 1: <RL | Imp 1: <RL | Imp 1: <RL | Imp 1: <RL | | Imp 1: <RL | Imp 1: <RL |
| Imp 4: <RL | Imp 4: <RL | Imp 4: 0.13% | Imp 4: 0.12% | Imp 4: 0.12% | Imp 4: 0.25% | | Imp 4: 0.14% | Imp 4: 0.30% |
| Imp 5: <RL | Imp 5: 0.11% | Imp 5: 0.14% | Imp 5: 0.17% | Imp 5: 0.17% | Imp 5: 0.26% | | Imp 5: 0.18% | Imp 5: 0.36% |
| Total: <RL | Total: 0.11% | Total: 0.27% | Total: 0.29% | Total: 0.29% | Total: 0.51% | | Total: 0.32% | Total: 0.66% |

TABELLE 7

Verunreinigungen in Formulierung 179/182

| | | 1 Monat | | 3 Monate | | | 6 Monate | |
|---|---|---|---|---|---|---|---|---|
| Initial | 25° C. | 40° C. | 5° C. | 25° C. | 40° C. | | 25° C. | 40° C. |
| Imp 1: <RL | Imp 1: <RL | Imp 1: <RL | Imp 1: <RL | Imp 1: <RL | Imp 1: <RL | | Imp 1: <RL | Imp 1: <RL |
| Imp 4: <RL | Imp 4: <RL | Imp 4: 0.16% | Imp 4: <RL | Imp 4: 0.13% | Imp 4: 0.25% | | Imp 4: 0.14% | Imp 4: 0.36% |
| Imp 5: <RL | Imp 5: 0.11% | Imp 5: 0.17% | Imp 5: 0.13% | Imp 5: 0.15% | Imp 5: 0.28% | | Imp 5: 0.18% | Imp 5: 0.41% |
| Total: <RL | Total: 0.11% | Total: 0.33% | Total: 0.13% | Total: 0.28% | Total: 0.53% | | Total: 0.32% | Total: 0.77% |

The quantity information provided as a percentage of the contamination is the proportion of the desired content of active substance in the involved formulations. The lower limit of the measuring values (reporting limit) of the individual contaminations is 0.1% because any values below are in the range of measuring inaccuracy. Aside from the contaminations as reported in Tables 6 and 7, no further contamination was detected above the "reporting limit" of 0.1%.

The results of this study clearly show that the TTS formulations demonstrate adequate stability.

The present invention refers, among others aspects, to the following subject-matters (1) to (17).

(1) A transdermal therapeutic system for administering of rivastigmine comprising the following components:
  a) a cover layer,
  b) a reservoir present on the cover layer, comprising a polymer matrix with the embedded active substance, and wherein the active substance is rivastigmine or a physiologically compatible salt, hydrate, solvate or derivatives thereof,
  c) an adhesive layer on the reservoir comprising a first polyisobutylene polymer of a mean molecular weight between 30,000 g/mol and 100,000 g/mol and a second polyisobutylene polymer of a mean molecular weight between 300,000 g/mol and 500,000 g/mol, and
  d) a removable layer present on the adhesive layer,
characterized in that the polymer matrix of the reservoir includes neither hydroxyl groups nor carboxyl groups.

(2) The transdermal therapeutic system according to subject-matter (1) wherein it does not contain any antioxidants.

(3) The transdermal therapeutic system according to subject-matter (1) or (2) wherein the reservoir contains 20 to 30 weight % active substance and 70 to 80 weight % polymer matrix in relation to the total weight of the reservoir.

(4) The transdermal therapeutic system according to any one of the subject-matters (1) to (3) wherein the adhesive layer additionally contains a gelatinizing agent and an emollient.

(5) The transdermal therapeutic system according to subject-matter (4) wherein the adhesive layer contains 60.0 to 74.9 weight % contact adhesive, 0.1 to 2.0 weight % gelatinizing agent and 25 to 39.9 weight % emollient in relation to the total weight of the adhesive layer.

(6) The transdermal therapeutic system according to any one of the subject-matters (1) to (5) wherein the polymer matrix comprises at least one polymer and/or copolymer selected from the group consisting of polyacrylates, acrylate-vinyl acetate copolymers, polyisobutylene, styrene-butadiene copolymers and mixtures thereof.

(7) The transdermal therapeutic system according to any one of the subject-matters (1) to (6) wherein the first polyisobutylene polymer has a mean molecular weight $M_V$ of approximately 40,000 g/mol, and the second polyisobutylene polymer has a mean molecular weight $M_V$ of approximately 40,000 g/mol.

(8) The transdermal therapeutic system according to any one of the subject-matters (1) to (7) wherein the weight ratio of the first polyisobutylene polymer in relation to the second polyisobutylene polymer is approximately 4:6.

(9) The transdermal therapeutic system according to any one of the subject-matters (1) to (8) wherein the gelatinizing agent $SiO_2$ is present in highly dispersed form or in form of pyrogenic silicic acid.

(10) The transdermal therapeutic system according to any one of the subject-matters (4) to (9) wherein the emollient is paraffin, neutral oil, mineral oil or polybutene or a mixture thereof.

(11) The transdermal therapeutic system according to any one of the subject-matters (1) to (10) wherein the area of the adhesive layer corresponds to the area of the reservoir.

(12) A transdermal therapeutic system for administering an active substance through the skin comprising:
  a) a cover layer;
  b) a reservoir located on the cover layer containing 20 to 30 weight % active substance and 70 to 80% polymer matrix in relation to the total weight of the reservoir, and wherein the polymer matrix consists essentially of an acrylate-vinyl acetate copolymer without hydroxyl groups and without carboxyl groups;
  c) an adhesive layer located on the reservoir that comprises 0.1 to 1 weight % silicone dioxide, 25 to 39.9 weight % paraffinum perliquidum (Ph. Eur.) and 60 to 79.9 weight % of a mixture of a polyisobutylene of a mean molecular weight $M_V$ of approximately 40,000 g/mol and polyisobutylene of a mean molecular weight $M_V$ of approximately 400,000 g/mol; and
  d) a removable layer located on the adhesive layer.

(13) A method for preparing a transdermal therapeutic system according to any one of the subject-matters (1) to (12) comprising
  i) preparing a component containing the reservoir made up of the cover layer and the reservoir, which is located on the side of the cover layer that is intended as the side to be directed toward the skin;
  ii) preparing a component containing the adhesive layer made up of the removable layer and the adhesive layer located on the removable layer; and
  iii) laminating to combine the components from i) and ii) so that in the end, in the cross-section of the completed TTS, the cover and removable layers constitute the outermost, opposite layers.

(14) The method according to subject-matter (13) comprising
  i) applying, with drying, if necessary, a film of a composition constituting the reservoir, if necessary, in form of a solution or dispersion in an expedient medium to the side of the cover layer that is to be directed toward the skin;
  ii) applying, with subsequent drying, if necessary, a film of a composition constituting the adhesive layer, if necessary, in the form of a solution or dispersion in an expedient medium, to the removable layer; and
  iii) laminating together the components from i) and ii), if necessary, removing the liner in order for the cover layer and the removable layer to constitute in the cross-section of the completed TTS the outermost, opposite layers.

(15) The method according to subject-matter (13) comprising
  i) applying, with drying, if necessary, a film of a composition constituting the reservoir, if necessary, in form of a solution or dispersion in an expedient medium to the side of the cover layer that is to be directed toward the skin and, if necessary, coating with a siliconized removable film (liner);
  ii) applying, with subsequent drying, if necessary, a film of a composition constituting the adhesive layer, if necessary, in the form of a solution or dispersion in an expedient medium, to the removable layer; and
  iii) laminating together the components from i) and ii), if necessary, removing the liner in order for the cover layer and the removable layer to constitute in the cross-section of the completed TTS the outermost, opposite layers.

(16) The use of a polymer or copolymer that contains neither hydroxyl groups nor carboxyl groups selected from the group consisting of polyacrylates, acrylate-vinyl acetate copolymers, polyisobutylene and styrene-butadiene copolymers for preparing transdermal therapeutic systems containing rivastigmine.

(17) The transdermal therapeutic system according to any one of the subject-matters (1) to (12) for treating Alzheimer's and Parkinson's dementia.

The subject-matters (1) to (17) can be combined with other embodied examples as described in the present application.

The invention claimed is:

1. A transdermal therapeutic system for administering an active substance through the skin comprising:
   a) a cover layer,
   b) a reservoir present on the cover layer, comprising a polymer matrix,
   c) an adhesive layer on the reservoir comprising a contact adhesive, and
   d) a removable layer present on the adhesive layer,
wherein the active substance is rivastigmine or a physiologically tolerable salt, hydrate, solvate or derivative thereof, and wherein the polymer matrix of the reservoir includes neither hydroxyl groups nor carboxyl groups.

2. The transdermal therapeutic system according to claim 1 wherein it does not contain any antioxidants.

3. The transdermal therapeutic system according to claim 1 wherein the reservoir contains 20 to 30 weight % active substance and 70 to 80 weight % polymer matrix in relation to the total weight of the reservoir.

4. The transdermal therapeutic system according to claim 1 wherein the adhesive layer additionally contains a gelatinizing agent and an emollient.

5. The transdermal therapeutic system according to claim 4 wherein the adhesive layer contains 60.0 to 74.9 weight % contact adhesive, 0.1 to 2.0 weight % gelatinizing agent and 25 to 39.9 weight % emollient in relation to the total weight of the adhesive layer.

6. The transdermal therapeutic system according to claim 1 wherein the polymer matrix comprises at least one polymer and/or copolymer selected from the group consisting of polyacrylates, acrylate-vinyl acetate copolymers, polyisobutylene, styrene-butadiene copolymers and mixtures thereof.

7. The transdermal therapeutic system according to claim 1 wherein the contact adhesive is polyisobutylene.

8. The transdermal therapeutic system according to claim 7 wherein the polyisobutylene is a mixture of two polyisobutylene polymers of different molecular weights.

9. The transdermal therapeutic system according to claim 8 wherein the first polyisobutylene polymer has a mean molecular weight $M_V$ of approximately 40,000 g/mol, and the second polyisobutylene polymer has a mean molecular weight $M_V$ of approximately 400,000 g/mol.

10. The transdermal therapeutic system according to claim 8 wherein the weight ratio of the first polyisobutylene polymer in relation to the second polyisobutylene polymer is approximately 4:6.

11. The transdermal therapeutic system according to claim 4 wherein the gelatinizing agent comprises $SiO_2$ having a particle size within the range of about 400 to about 1500 nm, which is in a dispersed form or in the form of pyrogenic silicic acid.

12. The transdermal therapeutic system according to claim 4 wherein the emollient is paraffin, neutral oil, mineral oil or a mixture thereof.

13. A transdermal therapeutic system for administering an active substance through the skin comprising:
   a) a cover layer,
   b) a reservoir located on the cover layer containing 20 to 30 weight % active substance and 70 to 80% polymer matrix in relation to the total weight of the reservoir, and wherein the polymer matrix consists essentially of an acrylate-vinyl acetate copolymer without hydroxyl groups and without carboxyl groups,
   c) an adhesive layer located on the reservoir that comprises 0.1 to 1 weight % silicone dioxide, 25 to 39.9 weight % paraffinum perliquidum (Ph. Eur.) and 60 to 79.9 weight % of a mixture of a polyisobutylene of a mean molecular weight $M_V$ of approximately 40,000 g/mol and a polyisobutylene of a mean molecular weight $M_V$ of approximately 400,000 g/mol, and
   d) a removable layer located on the adhesive layer.

14. A method for preparing a transdermal therapeutic system according to claim 13 comprising
   i) preparing a component containing the reservoir made up of the cover layer and the reservoir, which is located on the side of the cover layer that is intended as the side to be directed toward the skin,
   ii) preparing a component containing the adhesive layer made up of the removable layer and the adhesive layer located on the removable layer, and
   iii) laminating to combine the components from i) and ii) so that in the end, in a cross-section of the completed transdermal therapeutic system, the cover and removable layers constitute the outermost, opposite layers.

15. The method according to claim 14 comprising
   i) applying, with drying, if necessary, a film of a composition constituting the reservoir, if necessary, in form of a solution or dispersion in a suitable medium to the side of the cover layer that is to be directed toward the skin,
   ii) applying, with subsequent drying, if necessary, a film of a composition constituting the adhesive layer, if necessary, in the form of a solution or dispersion in a suitable medium, to the removable layer, and
   iii) laminating together the components from i) and ii) in order for the cover layer and the removable layer to constitute in the cross-section of the completed transdermal therapeutic system the outermost, opposite layers.

16. The transdermal therapeutic system according to claim 13 for treating Alzheimer's and Parkinson's dementia.

17. The transdermal therapeutic system according to claim 1 for treating Alzheimer's and Parkinson's dementia.

18. A method for preparing a transdermal therapeutic system according to claim 1 comprising
   i) preparing a component containing the reservoir made up of the cover layer and the reservoir, which is located on the side of the cover layer that is intended as the side to be directed toward the skin,
   ii) preparing a component containing the adhesive layer made up of the removable layer and the adhesive layer located on the removable layer, and
   iii) laminating to combine the components from i) and ii) so that in the end, in a cross-section of the completed transdermal therapeutic system, the cover and removable layers constitute the outermost, opposite layers.

19. The method according to claim 18 comprising
   i) applying, with drying, if necessary, a film of a composition constituting the reservoir, if necessary, in form of a solution or dispersion in a suitable medium to the side of the cover layer that is to be directed toward the skin,
   ii) applying, with subsequent drying, if necessary, a film of a composition constituting the adhesive layer, if necessary, in the form of a solution or dispersion in a suitable medium, to the removable layer, and
   iii) laminating together the components from i) and ii) in order for the cover layer and the removable layer to constitute in the cross-section of the completed transdermal therapeutic system the outermost, opposite layers.

20. Method for preparing a transdermal therapeutic system containing rivastigmine, comprising embedding the rivastigmine or a physiologically compatible salt, hydrate, solvate or derivatives thereof in a polymer or copolymer that contains neither free hydroxyl groups nor free carboxyl groups, selected from the group consisting of polyacrylates, acrylate-vinyl acetate copolymers, polyisobutylene and styrene-butadiene copolymers, optionally comprising stabilizing active substance rivastigmine in the transdermal therapeutic system and/or reducing the break-down of active substance rivastigmine in the transdermal therapeutic system.

* * * * *